(12) United States Patent
Brøndlund

(10) Patent No.: US 8,642,563 B2
(45) Date of Patent: Feb. 4, 2014

(54) MIXTURE AND INFUSION OR DRINK SOLUTION

(76) Inventor: Marianne Brøndlund, Harlev (DK)

(*) Notice: Subject to any disclaimer, the term of this patent is extended or adjusted under 35 U.S.C. 154(b) by 36 days.

(21) Appl. No.: 13/344,743

(22) Filed: Jan. 6, 2012

(65) Prior Publication Data

US 2012/0329734 A1    Dec. 27, 2012

(30) Foreign Application Priority Data

Jan. 7, 2011   (GB) .......................... 10 2011 008 090
Jun. 27, 2011  (GB) .......................... 10 2011 105 594

(51) Int. Cl.
   *A61K 31/70*        (2006.01)
(52) U.S. Cl.
   USPC ............................................................ 514/23

(58) Field of Classification Search
   USPC ............................................................ 514/23
   See application file for complete search history.

(56) References Cited

U.S. PATENT DOCUMENTS 6,875,456 B2 *   4/2005  Delest et al. ................... 426/63
2007/0020358 A1 * 1/2007  Mower ............................ 426/74

* cited by examiner

*Primary Examiner* — Elli Peselev
(74) *Attorney, Agent, or Firm* — Carter, DeLuca, Farrell & Schmidt, LLP

(57) ABSTRACT

The invention relates to a mixture, wherein the mixture contains ribose, alanine and glycine. The mixture furthermore can contain glutamine and one or more of the following substances: valine, leucine, isoleucine, 5-hydroxy-tryptophan, tryptophan, cysteine, serine. Alternatively or in addition, the mixture furthermore can contain asparagine, arginine, proline and lysine. The invention furthermore relates to a mixture which contains ribose, glycine, proline, lysine, arginine and asparagine.

43 Claims, No Drawings

MIXTURE AND INFUSION OR DRINK SOLUTION

This application claims priority to German Application No. 10 2011 008 090.2, filed Jul. 7, 2011 and German Application No. 10 2011 105 594.4, filed Jun. 27, 2011, the entireties of which are both hereby incorporated by reference.

This invention relates to a mixture, an infusion or drink solution, and to the use of a mixture as medicine.

In the past decades an increased demand for plant-based, natural and homeopathic drugs was noted, on the basis of which a multitude of diseases and symptoms are treated. These natural drugs often serve as supplement to the conventional treatment, for example to increase the well-being of the patient and to strengthen the immune system and the body. Such drugs often have minimal side effects and are in accord with a nature-conscious lifestyle, which is responsible for their growing popularity among patients.

It is the objective of the present invention to create a drug with natural ingredients, which can be used in the treatment of a multitude of diseases.

This is achieved by a mixture according to claim 1 or 10, by an infusion or drink solution according to claim 13, and by a use of a mixture according to claim 15. Advantageous embodiments can be taken from the sub-claims.

Accordingly, the invention relates to a mixture containing ribose, alanine and glycine. The mixture according to the invention serves for providing a drug which preferably exclusively contains natural ingredients.

In one embodiment, the ribose used is D-ribose. The same constitutes an important building block in the human body, for example in the RNA backbone and as constituent of adenosine and hence of ATP, ADP, AMP or cAMP.

In one embodiment, the alanine used is racemic (DL)-α-alanine. As constituent of infusion or drink solutions, alanine can be serve for parenteral nutrition.

As amino acid, glycine is an important constituent of almost all proteins and an important nodal point in the metabolism.

In this composition, a mixture according to the invention thus represents a novel combination of active ingredients, which strengthens various body functions and with a suitable administration and dosage can successfully be used for the treatment and the supportive treatment of a multitude of diseases.

In one embodiment, the relative mass ratio of ribose, alanine and glycine in the mixture according to the invention is A:B:C with $35<A<200$, $20<B<80$ and $1<C<40$. In a preferred embodiment, the relative mass ratio is A:B:C with $60<A<120$, $30<B<70$ und $2<C<20$, furthermore advantageously $50<A<90$, $30<B<50$ and $3<C<5$. A mass ratio of about 70:40:4 is particularly preferred.

In a first embodiment, the mixture furthermore can contain glutamine, in particular L-glutamine. Advantageously, the relative mass ratio of ribose, alanine, glycine and glutamine is A:B:C:D with $35<A<200$, $20<B<80$, $1<C<40$ and $20<D<80$, advantageously with $60<A<120$, $30<B<70$, $2<C<20$ and $30<D<60$, furthermore advantageously with $A=70$, $B=40$, $C=4$ and $D=50$.

In particular in the first embodiment, the mixture furthermore can contain one or more of the following substances: serine, valine, leucine, isoleucine, cysteine, 5-hydroxy-tryptophan, tryptophan. Advantageously, these substances, each are L-serine, L-valine, L-leucine, L-Isoleucine, L-cysteine, L-5-hydroxy-tryptophan, L-tryptophan.

When the mixture contains one or more of these substances, the relative mass ratio of ribose, alanine, glycine and the respective substance advantageously is A:B:C:D with $35<A<200$, $20<B<80$ and $1<C<40$, advantageously with $60<A<120$, $30<B<70$ and $2<C<20$, furthermore advantageously with $A=70$, $B=40$ and $C=4$, wherein D for the respective substance, when it is contained in the mixture, advantageously has the following value:

serine $10<D<150$, advantageously $40<D<120$, furthermore advantageously $D=100$;
valine $40<D<150$, advantageously $60<D<120$, furthermore advantageously $D=70$;
leucine $5<D<80$, advantageously $10<D<40$, furthermore advantageously $D=30$;
isoleucine $1<D<80$, advantageously $1<D<60$, furthermore advantageously $D=40$;
cysteine $1<D<150$, advantageously $5<D<120$, furthermore advantageously $D=100$;
5-hydroxy-tryptophan $1<D<100$, advantageously $10<D<60$, furthermore advantageously $D=50$;
tryptophan $1<D<100$, advantageously $10<D<60$, furthermore advantageously $D=50$;

The mixture can contain 5-hydroxy-tryptophan, tryptophan or mixtures of 5-hydroxy-tryptophan and tryptophan, wherein advantageously the total content 5-hydroxy-tryptophan and tryptophan is $1<D<100$, advantageously $10<D<60$, furthermore advantageously $D=50$.

In a second embodiment, the mixture furthermore can contain one or more of the following substances: asparagine, arginine, proline, lysine. In particular, the mixture can contain all of these substances. Advantageously, the substances are L-asparagine, L-arginine, L-proline and L-lysine.

When the mixture contains one or more of these substances, the relative mass ratio of ribose, alanine, glycine and the respective substance advantageously is A:B:C:D with $35<A<200$, $20<B<80$ and $1<C<40$, advantageously with $60<A<120$, $30<B<70$ and $2<C<20$, furthermore advantageously with $A=70$, $B=40$ and $C=4$, and for:

asparagine $1<D<100$, advantageously $10<D<80$, furthermore advantageously $20<=D<=70$;
arginine $1<D<100$, advantageously $2<D<60$, furthermore advantageously $4<=D<=40$;
proline $1<D<100$, advantageously $5<D<80$, furthermore advantageously $10<=D<=70$;
lysine $10<D<80$, advantageously $30<D<50$, furthermore advantageously $D=40$;

Advantageously, the mixture according to the second embodiment also contains the additional substances which are contained in the mixture according to the first embodiment, advantageously in the concentrations indicated for the first embodiment.

Advantageously, the mixture according to the invention contains other amino acids and/or sugars only in a mass ratio of less than 1:10 relative to the total content of ribose, alanine and glycine, furthermore advantageously of 1:100, furthermore advantageously of less than 1:1000. Preferably, the mixture according to the invention contains no other amino acids and/or sugars.

In one embodiment, the mixture according to the invention is a solid mixture, which contains the constituents as solids. At room temperature, ribose, alanine and glycine are present as solid, typically as white powder.

In one embodiment, the solid mixture according to the invention is a powdery mixture of the powdery constituents ribose, alanine and glycine as well as possibly further substances. In one embodiment, the solid mixture according to the invention substantially or exclusively consists of these constituents.

In one embodiment, the solid mixture according to the invention is provided in separate containers in a certain dosage. Suitable containers for example include paper bags, paper envelopes, plastic sleeves, plastic tubes or closed glass tubes.

In one embodiment, a container contains exactly one dosing unit, which contains between about 35 g and 200 g ribose, between about 20 g and 80 g alanine, and between about 1 g and 40 g glycine. This represents a suitable dosage in terms of the quantities and in particular the quantity ratios in the case of a further use for producing a medicine, for example by dissolution and possibly dilution.

A preferred quantity of ribose within one dosing unit lies between about 60 g and 120 g, advantageously between 50 g and 90 g. A preferred quantity of alanine within one dosing unit lies between about 30 g and 70 g, advantageously between 30 g and 50 g. A preferred quantity of glycine within one dosing unit lies between 2 g and 20 g, advantageously between 3 g and 5 g glycine.

In accordance with the first embodiment, the dosing units furthermore can contain one or more of the substances glutamine, serine, valine, leucine, isoleucine, cysteine, 5-hydroxy-tryptophan, tryptophan, in particular in a quantity such that the mixture in the dosing unit has one of the total compositions described above in detail.

In accordance with the second embodiment, the dosing units furthermore can contain one or more of the substances asparagine, arginine, proline, lysine, in particular in a quantity such that the mixture in the dosing unit has one of the total compositions described above in detail.

The substances also can be provided in several dosing units.

The mixture according to the invention in particular is suitable as medicine for the treatment or supportive treatment of cardiological diseases, pneumological diseases, neurodegenerative diseases, malignant osseous tumors, lymphogenic leukemia, autoimmune diseases, lupus erythematodes, degenerative bone diseases, osteoporosis, rheumatoid arthritis, lipopathies and/or diabetes mellitus as well as for resistance-breaking of antibiotic resistances of pathogens, in particular for resistance-breaking of multiple antibiotic resistances.

The first embodiment in particular is suitable as medicine for the treatment or supportive treatment of cardiological diseases, pneumological diseases, neurodegenerative diseases, malignant osseous tumors, lymphogenic leukemia, autoimmune diseases, lupus erythematodes, degenerative bone diseases, osteoporosis, rheumatoid arthritis, lipopathies and/or diabetes mellitus.

The second embodiment, however, advantageously is used for resistance-breaking of antibiotic resistances, in particular for resistance-breaking of multiple antibiotic resistances. Advantageously, the mixture is used in addition to a treatment with an antibiotic, in particular in addition to a treatment with several antibiotics, wherein the effectiveness of the antibiotic or the antibiotics is restored or at least improved by resistance-breaking by means of the mixture.

In one embodiment, the mixture according to the invention is a liquid mixture, which contains the constituents in aqueous solution. Ribose, alanine and glycine are easily soluble in water, whereby the same can easily be dissolved in water or aqueous solutions at room temperature.

In a preferred embodiment, a liquid mixture according to the invention contains the constituents in solution in water or an isotonic solution. In particular, energized water can be used, preferably energized water according to Mee-Hu. The use of other physiologically acceptable solutions also is conceivable.

In a preferred embodiment, a liquid mixture according to the invention contains between about 35 g/l and about 200 g/l of ribose, between about 20 g/l and about 80 g/l of alanine, between about 1 g/l and about 40 g/l of glycine. This represents a suitable dosage with regard to the concentrations and in particular the concentration ratios in a use as medicine or in. a further use for preparing a medicine for example by dilution.

A preferred concentration range for ribose lies between about 60 g/l and 120 g/l, in particular between 50 g/l and about 90 g/l. A preferred concentration range for alanine lies between about 30 g/l and 70 g/l, in particular between 30 g/l and about 50 g/l. A preferred concentration range for glycine lies between about 2 g/l and 20 g/l, in particular between 3 g/l and about 5 g/l.

Furthermore, the aqueous solution according to the first embodiment advantageously can contain one or more of the following substances: glutamine, serine, valine, leucine, isoleucine, cysteine, 5-hydroxy-tryptophan, tryptophan.

Preferred concentration ranges for the respective substances, as far as present in the aqueous solution, are as follows:

glutamine between 20 g/l and 80 g/l, advantageously between 30 g/l and 60 g/l, furthermore advantageously 50 g/l;

serine between 10 g/l and 150 g/l, advantageously between 40 g/l and 120 g/l, furthermore advantageously 100 g/l;

valine between 40 g/l and 150 g/l, advantageously between 60 g/l and 120 g/l, furthermore advantageously 70 g/l;

leucine between 5 g/l and 80 g/l, advantageously between 10 g/l and 40 g/l, furthermore advantageously 30 g/l;

isoleucine between 1 g/l and 80 g/l, advantageously between 1 g/l and 60 g/l, furthermore advantageously 40 g/l;

cysteine between 1 g/l and 150 g/l, advantageously between 5 g/l and 120 g/l, furthermore advantageously 100 g/l;

5-hydroxy-tryptophan between 1 g/l and 100 g/l, advantageously between 10 g/l and 60 g/l, furthermore advantageously 50 g/l;

tryptophan between 1 g/l and 100 g/l, advantageously between 10 g/l and 60 g/l, furthermore advantageously 50 g/l.

The mixture can contain 5-hydroxy-tryptophan, tryptophan or mixtures of 5-hydroxy-tryptophan and tryptophan, wherein advantageously the total concentration of 5-hydroxy-tryptophan and tryptophan is between 1 g/l and 100 g/l, advantageously between 10 g/l and 60 g/l, furthermore advantageously 50 g/l.

Furthermore, the aqueous solution according to the second embodiment advantageously can contain one or more of the following substances: asparagine, arginine, praline, lysine.

Preferred concentration ranges for the respective substances, as far as present in the aqueous solution, are as follows:

asparagine between 1 g/l and 100 g/l, advantageously between 10 g/l and 60 g/l, furthermore advantageously between 20 g/l and 70 g/l;

arginine between 1 g/l and 100 g/l, advantageously between 2 g/l and 60 g/l, furthermore advantageously between 4 g/l and 40 g/l;

proline between 1 g/l and 100 g/l, advantageously between 5 g/l and 80 g/l, furthermore advantageously between 10 g/l and 70 g/l;

lysine between 10 g/l and 80 g/l, advantageously between 30 g/l and 50 g/l, furthermore advantageously 40 g/l.

Advantageously, the aqueous solution according to the second embodiment also contains the substances contained in the aqueous solution according to the first embodiment in the concentration indicated there.

In a further alternative embodiment it can be provided that a liquid mixture according to the invention substantially or exclusively consists of the constituents ribose, alanine and glycine and water or a physiologically acceptable solution, in particular an isotonic solution. In particular, energized water can be used, preferably energized water according to Mee-Hu.

The mixture according to the invention in particular is suitable for the treatment or for providing a medicine, in particular an infusion or drink solution for the treatment or supportive treatment of various cardiological diseases, pneumological diseases, neurodegenerative diseases, malignant osseous tumors, lymphogenic leukemia, autoimmune diseases, lupus erythematodes, degenerative bone diseases, osteoporosis, rheumatoid arthritis, lipopathies and/or diabetes mellitus as well as for resistance-breaking of antibiotic resistances of pathogens, in particular for resistance-breaking of multiple antibiotic resistances.

The first embodiment in particular is suitable as medicine for the treatment or supportive treatment of cardiological diseases, pneumological diseases, neurodegenerative diseases, malignant osseous tumors, lymphogenic leukemia, autoimmune diseases, lupus erythematodes, degenerative bone diseases, osteoporosis, rheumatoid arthritis, lipopathies and/or diabetes mellitus.

The second embodiment, however, advantageously is used for resistance-breaking of antibiotic resistances, in particular for resistance-breaking of multiple antibiotic resistances. Advantageously, the medicine according the invention is used in addition to a treatment with an antibiotic, in particular in addition to a treatment with several antibiotics, wherein the effectiveness of the antibiotic or the antibiotics is restored or at least improved by resistance-breaking by means of the medicine according to the invention.

In accordance with a third embodiment, a mixture according to the invention comprises ribose, glycine, proline, lysine, arginine and asparagine. The mixture according to the invention serves for providing a drug which preferably exclusively contains natural ingredients.

In one embodiment, the ribose used is D-ribose. The same constitutes an important building block in the human body, for example in the RNA backbone and as constituent of adenosine and hence of ATP, ADP, AMP or cAMP.

As amino acid, glycine is an important constituent of almost all proteins and an important nodal point in the metabolism. Proline, lysine, arginine and asparagine likewise are important amino acids. Advantageously, L-glycine, L-proline, L-lysine, L-arginine and L-asparagine are used.

In this composition, a mixture according to the third embodiment of the present invention thus represents a novel combination of active ingredients, which strengthens various body functions and with a suitable administration and dosage can successfully be used for the treatment and for the supportive treatment of diseases.

In particular, the mixture according to the third embodiment of the present invention can be used for strengthening the connective tissue, the cartilages, the bones, the skin or the eyes or for the treatment or supportive treatment of diseases of the connective tissue, the cartilages, the bones, the skin or the eyes, or for the treatment of cellulite.

In a preferred embodiment, the relative mass ratio of ribose, glycine, proline, lysine, arginine and asparagine is A:B:C:D:E:F, with the following values:
- ribose: $35<A<200$, advantageously $60<A<120$, furthermore advantageously $A=70$;
- glycine: $1<B<40$, advantageously $5<B<20$, furthermore advantageously $B=10$;
- proline: $10<C<100$, advantageously $20<C<80$, furthermore advantageously $40<=C<=60$;
- lysine: $20<D<80$, advantageously $30<D<60$, furthermore advantageously $D=40$;
- arginine: $1<E<100$, advantageously $2<E<60$, furthermore advantageously $4<=E<=40$;
- asparagine: $10<F<80$, advantageously $20<F<50$, furthermore advantageously $F=30$.

In one embodiment, the mixture according to the invention contains other amino acids and/or sugars only in a mass ratio of less than 1:10 relative to the total content of ribose, glycine, proline, lysine, arginine and asparagine, furthermore advantageously of less than 1:100, furthermore advantageously of less than 1:1000. In particular, the mixture according to the invention can contain no other amino acids and/or sugars.

In one embodiment, the mixture according to the invention is a solid mixture, which contains the constituents as solids.

In one embodiment the solid mixture according to the invention is a powdery mixture of the powdery constituents ribose, glycine, proline, lysine, arginine and asparagine. In one embodiment, the solid mixture according to the invention substantially or exclusively consists of these constituents.

In one embodiment, the solid mixture according to the invention is provided in separate containers in a certain dosage. Suitable containers for example include paper bags, paper envelopes, plastic sleeves, plastic tubes or closed glass tubes.

In one embodiment, a container contains exactly one dosing unit, which dissolved in 1 liter of liquid provides the preferred concentration ranges indicated below with regard to a liquid mixture.

In one embodiment, the mixture according to the invention is a liquid mixture, which contains ribose, glycine, proline, lysine, arginine and asparagine in aqueous solution.

In a preferred embodiment, a liquid mixture according to the invention contains the constituents in solution in water or in an isotonic solution.

In particular, energized water can be used, preferably energized water according to Mee-Hu. The use of other physiologically acceptable solutions also is conceivable.

In a preferred embodiment, a liquid mixture according to the invention contains the respective substance in the following concentration:
- ribose between 35 g/l and 200 g/l, advantageously between $60<A<120$, furthermore advantageously $A=70$;
- glycine between 1 g/l and 40 g/l, advantageously between 5 g/l and 20 g/l furthermore advantageously $B=10$ g/l;
- proline between 10 g/l and 100 g/l, advantageously between 20 g/l and 80 g/l, furthermore advantageously between 40 g/l and 60 g/l;
- lysine between 20 g/l and 80 g/l, advantageously between 30 g/l and 60 g/l, furthermore advantageously $D=40$ g/l;
- arginine between 1 g/l and 100 g/l, advantageously between 2 g/l and 60 g/l, furthermore advantageously between 4 g/l and 40 g/l;
- asparagine between 10 g/l and 80 g/l, advantageously between 20 g/l and 50 g/l, furthermore advantageously $F=30$ g/l.

The mixture according to the third embodiment of the present invention can be used in particular for the treatment or for providing a medicine, in particular an infusion or drink solution for strengthening the connective tissue, the cartilages, the bones, the skin or the eyes or for the treatment or supportive treatment of diseases of the connective tissue, the cartilages, the bones, the skin or the eyes, or for the treatment of cellulite.

In all embodiments described above, the liquid mixture according to the invention can be a concentrate. To obtain a ready-to-use medicine, the same for example can further be diluted with water or physiologic saline. The above-mentioned mixing ratios in the concentrate are already chosen such that the desired quantity ratios are achieved by mere dilution. Furthermore, energized water according to Mee-Hu can be used for dilution.

In one embodiment, a liquid or solid mixture according to the invention furthermore contains at least one homeopathic active ingredient. Preferred homeopathic active ingredients comprise active ingredients selected from the group including *Magnesium phosphoricum*, Natrium pyruvicum, Natrium diethyloxalaceticum, Acidum citricum, Acidum cis-aconiticum, Barium oxalsuccinieum, Acidum α-ketoglutaricum, Acidum succinicum, Acidum fumaricum, Aqidum DL-malicum, *Strychnos nux-vomica*, Ubidecarenonum, Natrium pyruvicum, *Strychnos ignatii*, Hepar suis, *Silybum marianum*, Ren suis, *Calendula officinalis, Atropa belladonna, Aconitum napellus, Bellis perennis, Hypericum perforatum*, Echinacea, Echinacea purpurea, Symphytum officinale, *Matricaria recutita, Achillea millefolium*, Mercurius solubilis Hahnemanni, Hepar sulfuris, *Hamamelis virginiana,* Arnica montana and Zincum valerianicum.

This addition of the homeopathic active ingredients can establish or enhance the effect and curative power of a mixture according to the invention.

The invention furthermore relates to a method for providing a liquid mixture according to the invention, wherein a solid mixture according to the invention is dissolved in water or in another physiologically acceptable aqueous solution. Advantageously, energized water according to Mee-Hu is used.

In one embodiment, this dissolution process is effected at room temperature (about 21° C.) and/or while carefully stirring and/or under sterile conditions.

In one embodiment, a dosing unit of a solid mixture according to the invention is dissolved in between about 500 ml and about 1500 ml, preferably in between about 800 ml and about 1200 ml, and furthermore preferably in approximately or exactly 1000 ml water, physiologic saline or another physiologically acceptable aqueous solution. Advantageously, energized water according to Mee-Hu is used.

In one embodiment, one or more homeopathic active ingredients are added to the solution before and/or during and/or after the dissolution process.

Since not all of the possibly additionally provided substances are easily soluble and the total quantity of dissolved substances possibly can become large, the inventors of the present invention furthermore have developed special methods for preparing an aqueous solution.

The present invention comprises a method for preparing an aqueous solution, in which the solution is prepared by mixing two aliquots. A first aliquot is prepared by adding one or more of the substances valine, leucine, isoleucine, 5-hydroxy-tryptophan, tryptophan to an aqueous solution while stirring. Furthermore, a second aliquot is prepared by possibly adding glutamine and one or more of the substances cysteine, serine, alanine, glycine to a an aqueous solution while stirring. The first and the second aliquot then are mixed. Advantageously, mixing is effected in that the first aliquot is admixed to the second aliquot, advantageously by slowly adding the first aliquot while stirring continuously. Furthermore, ribose can be added to the solution obtained thereby. In particular, the method can be used for preparing an aqueous solution according to the first embodiment.

First of all, the hardly soluble substances are dissolved in the first aliquot, then possibly glutamine and the easily soluble substances are dissolved in a second aliquot, which then are mixed, wherein the ribose possibly is added last. Dissolution advantageously is effected while stirring continuously, and in particular for one substance after the other.

Advantageously, the above-mentioned substances are added in a quantity such that a mixture according to the first embodiment of the invention is obtained, as it was described above, in particular an aqueous solution according to the first embodiment, as it was described above.

In a further embodiment, one or more of the substances asparagine, arginine, proline, lysine are added to the prepared solution. In particular, the method can be used for preparing an aqueous solution according to the second embodiment.

The present invention furthermore comprises a method for preparing an aqueous solution, in which first one or more of the substances valine, leucine, isoleucine, 5-hydroxy-tryptophan, tryptophan, glutamine, cysteine, serine, alanine, glycine are dissolved at an elevated temperature of the aqueous solution whereupon the temperature of the aqueous solution is lowered and ribose and/or one or more of the substances asparagine, arginine, proline, lysine is dissolved at a lower temperature. Initially, a higher temperature therefore is utilized in accordance with the invention, in order to achieve a rather good solubility, whereas ribose is added at a lower temperature, so as not to damage the same.

Advantageously, one or more of the substances, valine, leucine, isoleucine, 5-hydroxy-tryptophan, tryptophan, glutamine, cysteine, serine, alanine, glycine are dissolved at a temperature of the aqueous solution between 50° C. and 80° C., advantageously between 60° C. and 75° C., furthermore advantageously at 70° C., and/or the ribose at a temperature between 20° C. and 50° C., advantageously between 30° C. and 45° C., furthermore advantageously at 40° C.

For preparing a solution according to the second embodiment, one or mare of the substances asparagine, arginine, proline, lysine then can possibly be added.

Advantageously, the above-described method of dissolving at different temperatures is combined with the above-described preparation from aliquots.

In particular, the first and the second aliquot are prepared and mixed under an elevated temperature. The mixed solution then is cooled, and the ribose is added. For preparing a solution according to the second embodiment, one or more of the substances asparagine, arginine, proline, lysine then can possibly be added.

The invention furthermore relates to an infusion or drink solution which contains the ingredients of a liquid mixture according to the invention in an about 1:10 to 1:100 dilution, advantageously a 1:20 to about 1:60 dilution. Preferably, an infusion or drink solution according to the invention contains these ingredients in an about 1:25 or about 1:50 dilution. As a basis for the infusion or drink solution, energized water according to Mee-Hu preferably is used. The use of other physiologically acceptable solutions also is conceivable. The infusions are suitable for parenteral or oral administration to a patient.

Depending on the desired treatment intensity and the condition of the patient, an attending physician can adapt the degree of dilution of the infusion within the limits of the invention.

In one embodiment, the infusion according to the invention contains at least one homeopathic active ingredient. Preferred homeopathic active ingredients comprise active ingredients selected from the group including *Magnesium phosphoricum*, Natrium pyruvicum, Natrium diethyloxalaceticum, Acidum citricum, Acidum cis-aconiticum, Barium oxalsuccinicum, Acidum α-ketoglutaricum, Acidum succinicum, Acidum fumaricum, Acidum DL-malicum, *Strychnos nux-vomica*, Ubidecarenonum, Natrium pyruvicum, *Strychnos ignatii*, Hepar suis, *Silybum marianum, Ren suis, Calendula officinalis*, Atropa bella-donna, *Aconitum napellus, Bellis perennis*, Hypericum perforatum, Echinacea, Echinacea purpurea, Symphytum officinale, *Matricaria recutita, Achillea millefolium*, Mercurius solubilis Hahnemanni, Hepar sulfuris, *Hamamelis virginiana*, Arnica montana and Zincum valerianicum.

This addition of the homeopathic active ingredients can establish or enhance the effect and curative power of an infusion according to the invention.

The invention furthermore relates to a method for providing an infusion or drink solution according to the invention by diluting a liquid mixture according to the invention in a base solution, preferably on the basis of energized water according to Mee-Hu.

In one embodiment, about 10 ml (between about 8 ml and about 12 ml) of a liquid mixture according to the invention are diluted in either about 250 ml or about 500 ml of an infusion base solution. As infusion or drink base solution preferably sterile water or an isotonic saline preferably is used (in particular energized water according to Mee-Hu is used for the infusion or drink base solution). The use of other physiologically acceptable solutions also is conceivable.

In one embodiment, one or more homeopathic active ingredients are added to the infusion before and/or during and/or after the dilution process.

The invention furthermore relates to the use of a mixture according to the invention as medicine and/or for preparing a medicine, preferably an infusion or drink solution, and furthermore preferably of an infusion or drink solution according to the invention.

Such medicine or an infusion or drink solution according to the invention, can be used in the sole treatment or as an addition to the conventional medical treatment. Its administration strengthens the body and the immune system, improves the well-being of the patient, and thus promotes healing.

What is preferred is the use of a mixture according to the first embodiment of the invention for preparing a medicine, preferably an infusion or as drink solution, for the treatment of diseases selected from the group including cardiological diseases, pneumological diseases, neurodegenerative diseases, malignant osseous tumors, lymphogenic leukemia, autoimmune diseases, lupus erythematodes, degenerative bone diseases, osteoporosis, rheumatoid arthritis, lipopathies and/or diabetes mellitus.

What is preferred is the use of a mixture according to the second embodiment of the invention for preparing a medicine, preferably an infusion or as drink solution, for resistance-breaking of antibiotic resistances of pathogens, in particular for resistance-breaking of multiple antibiotic resistances.

What is preferred is the use of a mixture according to the third embodiment of the present invention for preparing a medicine, preferably an infusion or as drink solution, for strengthening the connective tissue, the cartilages, the bones, the skin or the eyes or for the treatment or supportive treatment of diseases of the connective tissue, the cartilages, the bones, the skin or the eyes, or for the treatment of cellulite.

Further details and advantages of the invention can be taken from the following exemplary embodiments:

Exemplary Embodiment 1

In a packaging unit, for example a coated paper sachet, 70 g D-ribose, 40 g DL-α-alanine, 4 g glycine are provided in powder form.

The same are dissolved in 1 L isotonic saline, in particular on the basis of energized water according to Mee-Hu, at 21° C. while carefully stirring and under sterile conditions. There is obtained a concentrate with 70 g/l D-ribose, 40 g/l DL-α-alanine, 4 g glycine and 9 g/l NaCl, which is suitable and intended to be added to an infusion or drink solution in a corresponding dilution.

The following homeopathic ampoules of the firm Heel—Healthcare Designed by Nature are added to the concentrate: 10 ampoules of 1.1 ml Heel citric acid cycle, 10 ampoules of 1.1 ml *Nux vomica*-Injeel S, 5 ampoules of 1.1 ml Ubichinon-Injeel forte, 5 ampoules of 1.1 ml Acidum DL-malicum-Injeel, 5 ampoules of 1.1 ml Natrium pyruvicum-Injeel, 10 ampoules of 1.1 ml Ignatia-Injeel S, 10 ampoules of 1.1 ml Hepar suis-Injeel, 10 ampoules of 1.1 ml Carduus marianus-Injeel forte, 10 ampoules of 1.1 ml Ren suis-Injeel, 5 ampoules of 5 ml Traumeel S, 5 ampoules of 5 ml Belladonna-Homaccord and 10 ampoules of 1.1 ml Zincum valerianicum-Injeel.

10 ml of this concentrate are added to 250 ml or 500 ml water or physiologically acceptable solution, preferably 0.9% sodium chloride solution, wherein here advantageously energized water according to Mee-Hu is used, and intravenously or orally administered to the patient as an additional therapy in the treatment of cardiological diseases, pneumological diseases, neurodegenerative diseases, malignant osseous tumors, lymphogenic leukemia, autoimmune diseases lupus erythematodes, degenerative bone diseases, osteoporosis, rheumatoid arthritis lipopathies and/or diabetes mellitus.

Exemplary Embodiment 2

In a second exemplary embodiment the following quantities of substances can be dissolved in 1 L isotonic saline, in particular on the basis of energized water according to Mee-Hu, as follows:

The aqueous solution is divided among two vessels, so as to first prepare two aliquots:

1st aliquot (e.g. with 50% of the liquid):

At a temperature of the sodium chloride solution of 70° C., while continuously stirring, the hardly soluble substances are dissolved in the first aliquot:

30 g L-leucine, 40 g L-isoleucine, 50 g L-5-hydroxy-tryptophan or L-tryptophan or a mixture of the two;

2nd aliquot (e.g. with 50% of the liquid):

At a temperature of the sodium chloride solution of 70° C., while continuously stirring, first 50 g L-glutamine and then the easily soluble substances:

40 g DL-α-alanine, 4 g glycine, 100 g L-serine, 100 g L-cysteine are dissolved in the second aliquot.

The first aliquot then is stirred into the second aliquot, advantageously by slowly adding the first aliquot while stirring. Mixing can be effected at a temperature of the solutions of 70° C.

The temperature of the solution now is reduced to 40° C. and 70 g D-ribose is added.

The following homeopathic ampoules of the firm Heel—Healthcare Designed by Nature again are added to the concentrate thus produced: 10 ampoules of 1.1 ml Heel citric acid cycle, 10 ampoules of 1.1 ml *Nux vomica*-Injeel S, 5 ampoules of 1.1 ml Ubichinon-Injeel forte, 5 ampoules of 1.1 ml Acidum DL-malicum-Injeel, 5 ampoules of 1.1 ml Natrium pyruvicum-Injeel, 10 ampoules of 1.1 ml Ignatia-Injeel S, 10 ampoules of 1.1 ml Hepar suis-Injeel, 10 ampoules of 1.1 ml Carduus marianus-Injeel forte, 10 ampoules of 1.1 ml Ren suis-Injeel, 5 ampoules of 5 ml Traumeel S, 5 ampoules of 5 ml Belladonna-Homaccord and 10 ampoules of 1.1 ml Zincum valerianicum-Injeel.

10 ml of this concentrate again are added to 250 ml or 500 ml water or physiologically acceptable solution, preferably to 0.9% sodium chloride solution, wherein here as well energized water according to Mee-Hu advantageously is used.

Depending on the patient, alternative compositions can also be used, wherein ribose, alanine, glycine and possibly glutamine form a base mixture to which one or more of the substances serine, valine, leucine, isoleucine, cysteine, 5-hydroxy-tryptophan and tryptophan can be added.

Exemplary Embodiment 3

The third exemplary embodiment is based on a concentrate according to the second exemplary embodiment.

To 1 L concentrate, which is prepared as described above for the second exemplary embodiment, 20 g, 40 g or 70 g L-asparagine, 4 g, 10 g, 30 g or 40 g L-arginine, 10 g, 30 g or 70 g L-proline and 40 g L-lysine furthermore is admixed while carefully stirring and under sterile conditions.

There is obtained a concentrate which is suitable and intended to be added to an infusion or drink solution in a corresponding dilution.

The following homeopathic ampoules of the firm Heel—Healthcare Designed by Nature again are added to the concentrate thus produced: 10 ampoules of 1.1 ml Heel citric acid cycle, 10 ampoules of 1.1 ml *Nux vomica*-Injeel S, 5 ampoules of 1.1 ml Ubichinon-Injeel forte, 5 ampoules of 1.1 ml Acidum DL-malicum-lnjeel, 5 ampoules of 1.1 ml Natrium pyruvicum-Injeel, 10 ampoules of 1.1 ml Ignatia-Injeel S, 10 ampoules of 1.1 ml Hepar suis-lnjeel, 10 ampoules of 1.1 ml Carduus marianus-Injeel forte, 10 ampoules of 1.1 ml Ren suis-Injeel, 5 ampoules of 5 ml Traumeel S, 5 ampoules of 5 ml Belladonna-Homaccord and 10 ampoules of 1.1 ml Zincum valerianicum-Injeel.

10 ml of this concentrate again are added to 250 ml or 500 ml water or physiologically acceptable solution, preferably to 0.9% sodium chloride solution, wherein here as well energized water according to Mee-Hu advantageously is used.

The resulting solution can be used as drink or infusion solution for resistance-breaking of antibiotic resistances, in particular for resistance-breaking of multiple antibiotic resistances. Advantageously, the mixture is used in addition to a treatment with an antibiotic, in particular in addition to a treatment with several antibiotics, wherein the effectiveness of the antibiotic or the antibiotics is restored or at least improved by resistance-breaking by means of the mixture.

Exemplary Embodiment 4

In one or more packaging units, for example in a coated paper sachet, 70 g D-ribose, 10 g glycine, 40 g or 60 g L-proline, 40 g lysine, 4 g, 7 g, 10 g, 30 g or 40 g L-arginine and 30 g L-asparagine are provided in powder form.

The same are dissolved in 1 L isotonic saline, in particular on the basis of energized water according to Mee-Hu, at 21° C. while carefully stirring and under sterile conditions. There is obtained a concentrate which is suitable and intended to be added to an infusion or drink solution in a corresponding dilution.

The following homeopathic ampoules of the firm Heel—Healthcare Designed by Nature again are added to the concentrate thus produced: 10 ampoules of 1.1 ml Heel citric acid cycle, 10 ampoules of 1.1 ml *Nux vomica*-Injeel S, 5 ampoules of 1.1 ml Ubichinon-Injeel forte, 5 ampoules of 1.1 ml Acidum DL-malicum-Injeel, 5 ampoules of 1.1 ml Natrium pyruvicum-Injeel, 10 ampoules of 1.1 ml Ignatia-Injeel S, 10 ampoules of 1.1 ml Hepar suis-Injeel, 10 ampoules of 1.1 ml Carduus marianus-Injeel forte, 10 ampoules of 1.1 ml Ren suis-Injeel, 5 ampoules of 5 ml Traumeel S, 5 ampoules of 5 ml Belladonna-Homaccord and 10 ampoules of 1.1 ml Zincum valerianicum-Injeel.

10 ml of this concentrate again are added to 250 ml or 500 ml water or physiologically acceptable solution, preferably to 0.9% sodium chloride solution, wherein here as well energized water according to Mee-Hu advantageously is used.

The resulting solution can be used as drink or infusion solution for strengthening the connective tissue, the cartilages, the bones, the skin or the eyes or for the treatment or supportive treatment of diseases of the connective tissue, the cartilages, the bones, the skin or the eyes, or for the treatment cellulite.

The invention claimed is:

1. A liquid mixture comprising an aqueous solution of 60 to 120 g/l of ribose, 30 to 70 g/l of alanine, 2 to 20 g/l of glycine and 30 to 60 g/l of glutamine.

2. The mixture according to claim 1, wherein the ribose is D-ribose and the alanine is DL-α-alanine and the relative mass ratio of ribose, alanine and glycine is A:B:C with $35<A<200$, $20<B<80$ and $1<C<40$.

3. The mixture according to claim 1, wherein the relative mass ratio of ribose, alanine, glycine and glutamine is A:B:C:D with $35<A<200$, $20<B<80$, $1<C<40$ and $20<D<80$
wherein the mixture furthermore contains one or more of the following substances:
serine, valine, leucine, isoleucine, cysteine, 5-hydroxy-tryptophan, and tryptophan.

4. The mixture further according to claim 3, wherein the mixture contains one or more of the following substances: asparagine, arginine, proline, lysine,
wherein asparagine, arginine, proline and lysine are each designated D' and the relative mass ratio of ribose, alanine, glycine and
D' is A:B:C:D' with $35<A<200$, $20<B<80$ and $1<C<40$, and for:
asparagine $1<D'<100$;
arginine $1<D'<100$;
proline $1<D'<100$;
lysine $10<D'<80$.

5. The mixture according to claim 1, wherein the mixture contains
between 60 g/l and 120 g/l of ribose,
between 30 g/l and 70 gl of alanine,
2 g/l and 20 g/l of glycine,
glutamine 50 g/l further contains;
serine between 10 g/l and 150 g/l;
valine between 40 g/l and 150 g/l;
leucine between 5 g/l and 80 g/l;
isoleucine between 1 g/l and 80 g/l;
cysteine between 1 g/l and 150 g/l;
5-hydroxy-tryptophan between 1 g/l and 100 g/l; and
tryptophan between 1 g/l and 100 g/l.

6. The mixture according to claim 4, wherein the mixture contains
between 60 g/l and 120 g/l of ribose,
between 30 g/l and 70 g/l of alanine,
between 2 g/l and 20 g/l of glycine, arginine between 1 g/l and 100 g/l;
asparagine between 1 g/l and 100 g/l;
proline between 1 g/l and 100 g/l;
lysine between 10 g/l and 80 g/l.

7. A mixture consisting essentially of ribose, glycine, proline, lysine, arginine and asparagine having a relative mass ratio of A:B:C:D:E:F, with the following values: $35<A<200$, $1<B<40$, $10<C<100$, $20<D<80$, $1<E<100$ and $10<F<80$.

8. The mixture according to claim 7, wherein the relative mass ratio of ribose, glycine, proline, lysine, arginine and asparagine is A:B:C:D:E:F, with the following values:
$60<A<120$;
$5<B<20$;
$20<C<80$;
$30<D<60$;
$2<E<60$;
$20<F<50$.

9. The mixture according to claim 8, wherein the mixture is a liquid mixture which contains ribose, glycine, proline, lysine, arginine and asparagine in aqueous solution, wherein the aqueous solution
contains ribose, glycine, proline, lysine, arginine and asparagine in the following concentration:
ribose between 35 g/l and 200 g/l;
glycine between 1 g/l and 40 g/l;
proline between 10 g/l and 100 g/l;
lysine between 20 g/l and 80 g/l;
arginine between 1 g/l and 100 g/l;
asparagine between 10 g/l and 80 g/l.

10. A method for preparing an aqueous solution according to claim 5, wherein
a first aliquot is prepared by adding one or more of the substances valine, leucine, isoleucine, 5-hydroxy-tryptophan, tryptophan to an aqueous solution while stirring,
a second aliquot is prepared by adding glutamine and one or more of the substances cysteine, serine, alanine, glycine to an aqueous solution while stirring,
whereupon the first aliquot is admixed to the second aliquot,
wherein ribose is added to the solution obtained thereby, and
wherein asparagine, arginine, proline, lysine are added to the solution.

11. A method for preparing an aqueous solution according to claim 10, wherein first one or more of the substances valine, leucine, isoleucine, 5-hydroxy-tryptophan, tryptophan, glutamine, cysteine, serine, alanine, glycine are dissolved at an elevated temperature of the aqueous solution, whereupon the temperature of the aqueous solution is lowered and ribose is dissolved at a lower temperature, wherein one or more of the
substances valine, leucine, isoleucine, 5-hydroxy-tryptophan, tryptophan, glutamine, cysteine, serine, alanine, glycine are dissolved at a temperature of the
aqueous solution between 50° C. and 80° C. and the ribose is dissolved at a temperature between 20° C. and 50° C., wherein furthermore one or more of asparagine, arginine, proline, lysine are added.

12. An infusion or drink solution comprising a liquid mixture according to claim 5 in a 1:10 to 1:100 dilution.

13. The mixture according to claim 1, wherein the mixture additionally contains at least one homeopathic ingredient.

14. A method for preparing an aqueous solution according to claim 6, wherein
a first aliquot is prepared by adding one or more of the substances Valine, leucine, isoleucine, 5-hydroxy-tryptophan, tryptophan to an aqueous solution while stirring,
a second aliquot is prepared by adding glutamine and one or more of the substances cysteine, serine, alanine, glycine to an aqueous solution while stirring,
whereupon the first and the second aliquot are mixed,
wherein ribose is added to the solution obtained thereby, and
wherein furthermore one or more of the substances asparagine, arginine, proline, lysine are added to the solution.

15. An infusion or drink solution comprising a liquid mixture according to claim 6 in a 1:10 to 1:100 dilution.

16. An infusion or drink solution comprising a liquid mixture according to claim 11 in a 1:10 to 1:100 dilution.

17. The mixture according to claim 2, wherein the relative mass ratio of A:B:C is $60<A<120$, $30<B<70$ and $2<C<20$.

18. The mixture according to claim 17, wherein the relative mass ratio of A is 70, B is 40 and C is 4.

19. The mixture according to claim 3, wherein A:B:C:D is $60<A<120$, $30<B<70$, $2<C<20$ and $30<D<60$.

20. The mixture according to claim 19, wherein A is 70, B is 40, C is 4 and D is 50.

21. The mixture according to claim 1, wherein the mass ratio of serine is $10<\text{serine}<150$, the mass ratio of valine is $40<\text{valine}<150$; the mass ratio of leucine is $5<\text{leucine}<80$; the mass ratio of isoleucine is $1<\text{isoleucine}<80$; the mass ratio of cysteine is $1<\text{cysteine}<150$; the mass ratio of 5-hydroxy-tryptophan is $1<\text{5-hydroxy-tryptophan}<100$; and the mass ratio of tryptophan is $1<\text{5-hydroxy-tryptophan}<100$.

22. The mixture according to claim 21, wherein the mass ratio of serine is $40<\text{serine}<120$, the mass ratio of valine is $60<\text{valine}<120$; the mass ratio of leucine is $10<\text{leucine}<40$; the mass ratio of isoleucine is $1<\text{isoleucine}<60$; the mass ratio of cysteine is $51<\text{cysteine}<120$; the mass ratio of 5-hydroxy-tryptophan is $10<\text{5-hydroxy-tryptophan}<60$; and the mass ratio of tryptophan is $10<\text{5-hydroxy-tryptophan}<60$.

23. The mixture according to claim 22, wherein the mass ratio of serine is 100; the mass ratio of valine is 70; the mass ratio of leucine is 30; the mass ratio of isoleucine is 40; the mass ratio of cysteine is 100; the mass ratio of 5-hydroxy-tryptophan is 50; and the mass ratio of tryptophan is 50.

24. The mixture according to claim 4 wherein A is between 60 and 120, B is between 30 and 70, C is between 2 and 20.

25. The mixture according to claim 4 wherein A is 70, B is 40 and C is 4.

26. The mixture according to claim 4 wherein asparagine is $10<D'<80$; arginine $2<D'<60$; proline $5<D<80$; and lysine $30<D'<50$.

27. The mixture according to claim 26 wherein asparagine is between 20 and 70, arginine is between 4 and 40, proline is between 10 and 70 and lysine is 40.

28. The mixture according to claim 5, wherein the mixture contains serine between 40 g/l and 120 g/l; valine between 60 g/l and 120 g/l; leucine between 10 g/l and 40 g/l; isoleucine: between 1 g/l and 60 g/l; cysteine between 5 g/l and 120 g/l; 5-hydroxy-tryptophan between 10 g/l and 60 g/l; tryptophan between 10 g/l and 60 g/l.

29. The mixture according to claim 28, wherein the mixture contains 100 g/l serine, 70 valine, 30 g/l leucine, 40 g/l isoleucine, 100 g/l cysteine, 50 g/l 5-hydroxy-tryptophan and 50 g/l tryptophan.

30. The mixture according to claim 6, wherein the mixture contains arginine between 2 g/l and 60 g/l; asparagine between 10 g/l and 60 g/l; proline between 5 g/l and 80 g/l; and lysine between 30 g/l and 50 g/l.

31. The mixture according to claim 30, wherein the mixture contains arginine between 4 g/l and 40 g/l asparagine between 20 g/l and 70 g/l, proline between 10 g/l and 70 and lysine 40 g/l.

32. The mixture according to claim 8, wherein A is 70, B is 10, C is 40<=C<=60, D is 40, E is 40 and F is 30.

33. The mixture according to claim 9, wherein the mixture contains glycine between 5 g/l and 20 g/l; proline 20 g/l and 80 g/l; lysine between 30 g/l and 60 g/l; arginine between 2 g/l and 60 g/l; and asparagine between 20 g/l and 50 g/l.

34. The mixture according to claim 33, wherein glycine is 10 g/l; proline between 40 g/l and 60 g/l; lysine is 40 g/l; arginine is between 4 g/l; and 40 g/l; and asparagine is 30 g/l.

35. The infusion or drink solution according to claim 12 wherein the liquid, mixture is in a 1:25 or 1:50 dilution.

36. The infusion or drink solution according to claim 15 wherein the liquid mixture is in a 1:25 or 1:50 dilution.

37. The infusion or drink solution according to claim 16 wherein the liquid mixture is in a 1:25 or 1:50 dilution.

38. A method for decreasing bacterial resistance to antibiotics comprising contacting antibiotic resistant bacteria with a mixture comprising D-ribose, DL-alanine, L-glycine and L-glutamine in an amount sufficient to decrease the bacteria's resistance to antibiotics.

39. The method for decreasing bacterial resistance to antibiotics according to claim 38 wherein the mixture comprises an aqueous solution of 60 to 120 g/l of ribose, 30 to 70 of alanine, 2 to 20 g/l of glycine, 30 to 60 g/l of glutamine.

40. The method for decreasing bacterial resistance to antibiotics according to claim 38, wherein the mixture further comprises serine, valine, leucine, isoleucine, tryptophane, asparagine, arginine, proline and lysine.

41. A method for decreasing bacterial resistance to antibiotics in a patient having an antibiotic-resistant bacterial infection comprising administering to the patient a mixture comprising ribose, alanine, glycine and glutamine in an amount sufficient to decrease the bacteria's resistance to antibiotics.

42. The method for decreasing bacterial resistance to antibiotics in a patient having an antibiotic-resistant bacterial infection according to claim 40, wherein the mixture comprises an aqueous solution of 60 to 120 g/l of ribose, 30 to 70 of alanine, 2 to 20 of glycine and 30 to 60 g/l of glutamine.

43. The method for decreasing bacterial resistance to antibiotics in a patient having an antibiotic-resistant bacterial infection according to claim 41, wherein the mixture further comprises, and serine, valine, leucine, isoleucine, tryptophane, asparagine, arginine, proline and lysine.

* * * * *